United States Patent [19]

Welton

[11] Patent Number: 4,885,309

[45] Date of Patent: Dec. 5, 1989

[54] THERAPEUTIC TREATMENT OF LEUKOTRIENE-MEDIATED DERMAL INFLAMMATION BY TOPICAL ADMINISTRATION OF 3,4-DIHYDRO-2H-1-BENZOPYRAN DERIVATIVES

[75] Inventor: Ann F. Welton, West Caldwell, N.J.

[73] Assignee: Hoffmann-La Roche Inc., Nutley, N.J.

[21] Appl. No.: 893,076

[22] Filed: Aug. 1, 1986

[51] Int. Cl.$^4$ .............................................. A61K 31/35
[52] U.S. Cl. .................................. 514/456; 514/861; 514/863; 514/887
[58] Field of Search ....................... 514/456, 863, 887; 549/405

[56] References Cited

U.S. PATENT DOCUMENTS

| | | | |
|---|---|---|---|
| 3,629,290 | 12/1971 | Calras et al. | 260/345.2 |
| 4,546,194 | 10/1985 | Miyano et al. | 549/401 |
| 4,565,882 | 1/1986 | Miyano et al. | 549/394 |
| 4,617,407 | 10/1986 | Young et al. | 549/462 |

FOREIGN PATENT DOCUMENTS

| | | |
|---|---|---|
| 139809 | 5/1985 | European Pat. Off. . |
| 0140684 | 5/1985 | European Pat. Off. . |
| 0150447 | 8/1985 | European Pat. Off. . |
| 84/4519 | 12/1984 | South Africa . |

OTHER PUBLICATIONS

7-Hydroxychroman and Its 6-Acetyl Compound,-P. Naylor et al., 1190–1193 (1957).
Some New Coumarins and Chromones and Their Ultraviolet Absorption Spectra, C. R. Jacobson et al., J. Org. Chem. 18, 1117 (1953).
Benzopyrones, Part II., 7-Hydroxy-4-Oxochromen-2-Carboxylic Acid and Some of Its Derivatives, G. Barker et al., J. Chem. Soc. (1970).
Pharmacologically Active 4-Oxo-4H-Chromen-2-Carboxylic Acids, Part II., The Synthesis of 4-Oxo-4H-Chromen-2-Carboxylic Acids Containing a Fused Imidazole or Oxazole Ring, A. O. Fitton et al., J. Chem. Soc. (1970).

Primary Examiner—Leonard Schenkman
Attorney, Agent, or Firm—Jon S. Saxe; Bernard S. Leon; Richard J. Mazza

[57] ABSTRACT

The compound 6-acetyl-7-[5-(4-acetyl-3-hydroxy-2-propylphenoxy)pentyloxy]-3,4-dihydro-24-1-benzopyran-2-carboxylic acid, as well as its enantiomers, salts and lower alkyl esters, are useful in topically administrable dosage forms for the treatment of leukotriene-mediated dermal inflammations, such as psoriasis. These compounds can be formulated into creams, ointments, lotions, gels and other types of compositions suitable for applying on the skin.

9 Claims, 3 Drawing Sheets

VASCULAR PERMEABILITY TEST

TIME COURSE-GUINEA PIG SKIN

TIME COURSE-RAT SKIN

THERAPEUTIC TREATMENT OF LEUKOTRIENE-MEDIATED DERMAL INFLAMMATION BY TOPICAL ADMINISTRATION OF 3,4-DIHYDRO-2H-1-BENZOPYRAN DERIVATIVES

BACKGROUND OF THE INVENTION

The present invention relates to the use of 6-acetyl-7-[5-(4-acetyl-3-hydroxy-2-propylphenoxy)-pentyloxy]-3,4-dihydro-2H-1-benzopyran-2-carboxylic acid, as well as enantiomers, salts and lower alkyl esters thereof, as anti-inflammmatory agents in the topical therapeutic treatment of leukotriene-mediated dermal inflammations, including psoriasis.

Psoriasis is a chronic skin condition characterized by increased epidermal cell turnover leading to scaling of the lesional skin, migration of neutrophils into the lesional dermis and epidermis, and dilation and increased permeability of the blood vessels in the affected area which often results in abnormal redness (erythema) and watery swelling (edema).

A number of different treatments have become available for this disease. Topical treatments generally employ corticosteroids or tar preparations, the latter of which are sometimes utilized in conjunction with ultraviolet light radiation. Systemic therapies which make use of corticosteroids are also known, and other non-topical anti-psoriatic agents include methotrexate, hydroxyurea and etretinate.

Other forms of inflammatory dermatosis such as eczema and atopic dermatitis are characterized by many of these same or similar symptoms.

SUMMARY OF THE INVENTION

The present invention concerns, in one of its aspects, a method for treating leukotriene-mediated dermal inflammations by the topical administration of an effective anti-inflammatory amount of 6-acetyl-7-[5-(4-acetyl-3-hydroxy-2-propylphenoxy)pentyloxy]-3,4-dihydro-2H--benzopyran-2-carboxylic acid, or an enantiomer, salt or lower alkyl ester thereof. The invention also concerns, as another aspect, topical compositions which incorporate the above-mentioned anti-inflammatory agent and are useful in the above-mentioned method.

By "topical" it is meant that these compounds are administered by directly contacting them with the skin at the diseased site or sites for the exertion of a therapeutic action. This is done most conveniently by incorporating the compound into a suitable pharmaceutical carrier and manually applying it to the affected area, as will be described in greater detail further on in this disclosure.

The compounds and compositions of this invention can be used to effectively treat various leukotriene-mediated dermal inflammatory conditions, such as psoriasis, dermatitis and eczema.

The same compounds involved here have been previously disclosed for other purposes in published South African patent application 2A 8404519, Dec. 24, 1984, and in particular for antiallergic uses, including asthma treatment. Still other dihydrobenzopyran compounds have been described in European patent publication Nos. 0139809 (May 8, 1985) and 0150447 (June 7, 1985) as leukotriene antagonists useful for treating allergies, as well as inflammatory conditions such as rheumatoid arthritis. The present invention, on the other hand, is based on the discovery that the particular compounds described here can be used topically to treat dermal inflammations and are more potent than other compounds in the same series for that purpose.

The term "leukotriene-mediated" is used to mean that the substance leukotriene is actively involved in the causation of the dermal inflammatory condition or in the manifestation of its symptoms, or both.

DETAILED DESCRIPTION OF THE INVENTION

Figure 1:
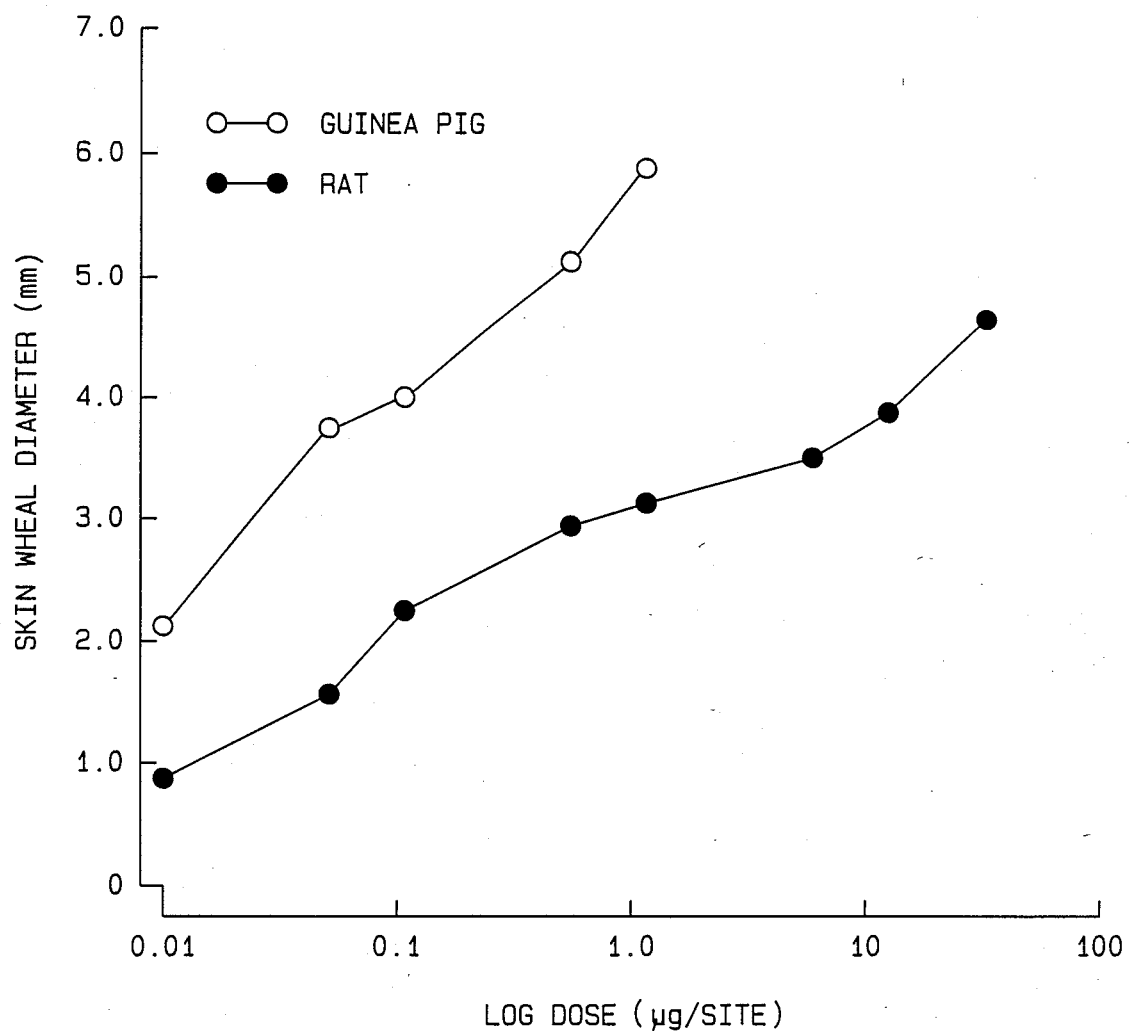

The anti-inflammatory compounds useful in the practice of the present invention have the formula

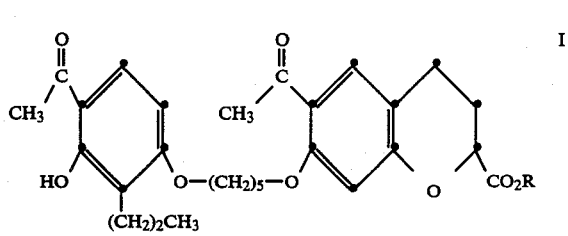

in which R is hydrogen or lower alkyl.

The term "lower alkyl" is used in this disclosure to refer to a straight or branched chain saturated hydrocarbon containing 1 to 7 carbon atoms, for example, methyl, ethyl, propyl, isopropyl, butyl, t-butyl, neopentyl, pentyl, hexyl and heptyl.

The compounds of formula I of this invention can be prepared in accordance with Reaction Scheme I, as follows:

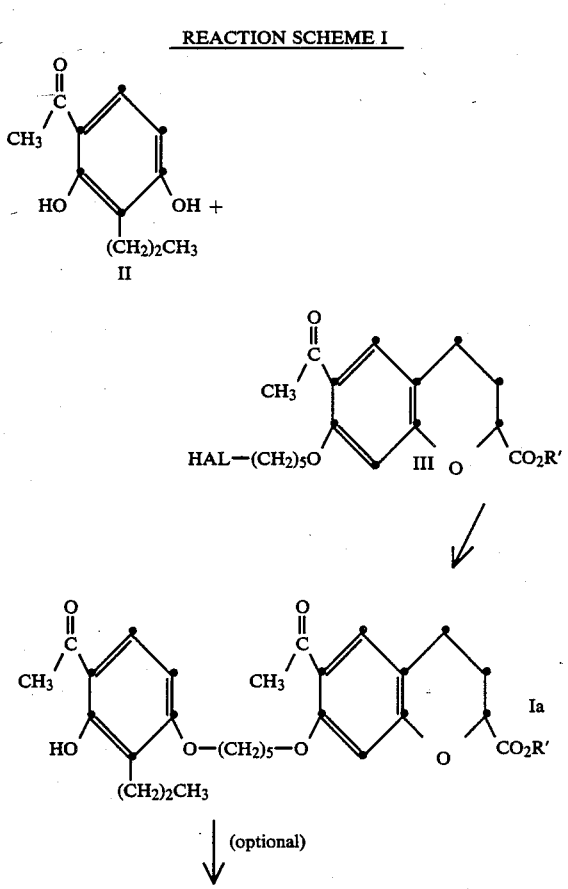

-continued
REACTION SCHEME I

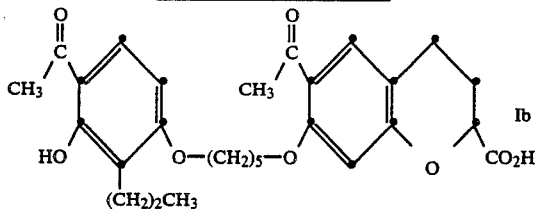

in which R' is lower alkyl and is as defined above for the compounds of formula I.

As used throughout this disclosure, the terms "HAL" and "halogen" refer to all the halogens, that is, bromine, chlorine, fluorine and iodine, although among these, bromine, chlorine and iodine are preferred.

In Reaction Scheme I, the reaction of a compound of formula II, which is a known compound or can be prepared according to known procedures, with a compound of formula III, to yield the compound of formula Ia, is carried out under anhydrous conditions in an inert solvent, for example, acetone, acetonitrile, methyl ethyl ketone, diethyl ketone, dimethylformamide, or the like. The reaction is conducted at the reflux temperature of the reaction mixture, preferably at a temperature in the range from about 70° to about 100° C., and in the presence of an acid acceptor, such as potassium carbonate, or the like. The preferred solvent is a mixture of acetone and dimethylformamide. The resulting compound of formula Ia can be recovered using conventional methods, for example, crystallization, chromatography, or the like.

If desired, the compound of formula Ia, which itself is useful in the described method of this invention, can be converted to the compound of formula Ib by hydrolysis. The hydrolysis is carried out with an alkali metal hydroxide, for example, lithium hydroxide, sodium hydroxide, potassium hydroxide, or the like, in a mixture of water and a water miscible solvent, for example, methanol, ethanol, tetrahydrofuran, or the like, at a temperature in the range from about room temperature (for example, 20° to 25° C.) to the reflux temperature. The resulting compound of formula Ib of this invention can be recovered by conventional methods, such as extraction, crystallization, chromatography, or the like.

This invention can also be practiced with use of pharmaceutically acceptable salts of the compounds of formula I, when R is hydrogen. These salts can be prepared by reacting an acid of formula I or an enantiomer thereof with a base having a non-toxic, pharmacologically and pharmaceutically acceptable cation. In general, any base which will form a salt with a carboxylic acid and whose pharmacological properties will not cause an adverse physiological effect when absorbed by a warm-blooded animal is considered as being within the scope of the invention. Suitable bases thus include, for example, alkali metal and alkaline earth metal hydroxides or carbonates, such as, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, basic amino acids such as lysine, and the like. The pharmaceutically acceptable salts thus produced are the functional equivalent of the corresponding 3,4-dihydro-H-1-benzopyran acid of formula I and its enantiomers and one skilled in the art will appreciate that, to the extent that the salts of the invention are useful in therapy, the variety of salts encompassed by this invention are limited only by the criterion that the bases employed in forming the salts be both non-toxic and physiologically acceptable.

The intermediates of formula III used for the preparation of the compounds of formula I can be prepared according to reaction Scheme II, as follows:

REACTION SCHEME II

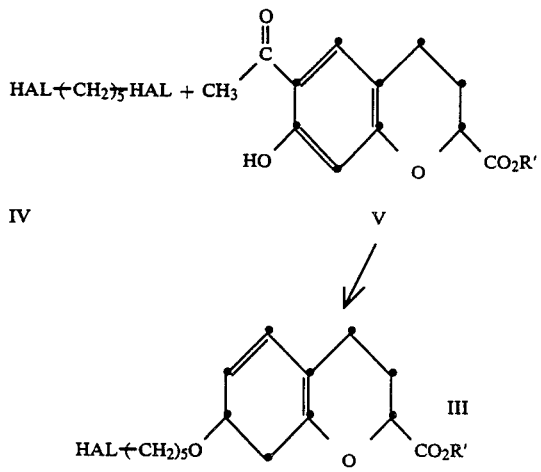

in which HAL and R' are as defined above.

In Reaction Scheme II, the reaction of a compound of formula IV, which itself is a known compound or can be prepared according to known procedures, with a compound of formula V, to yield a compound of formula III, is carried out in an inert organic solvent such as dimethylformamide, acetone, methyl ethyl ketone, acetonitrile, or the like, preferably acetonitrile. The reaction is conducted in the presence of a base, for instance, an alkali metal carbonate such as potassium carbonate, sodium carbonate, or the like, or, alternatively, an alkali metal hydride such as sodium hydride or the like, at a temperature in the range from about 20° to 150° C., preferably room temperature (for example, 20° to 25° C.). The resulting compound of formula III can be recovered utilizing conventional methods, such as crystallization, extraction, chromatography, or the like.

The intermediate of formula V used for the preparation of the compounds of formula III can be prepared according to Reaction Scheme III, as follows:

REACTION SCHEME III

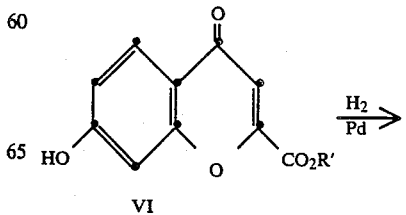

-continued
REACTION SCHEME III

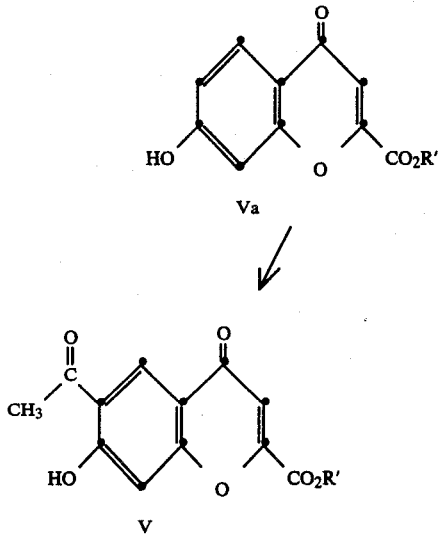

in which R' is as defined above.

In Reaction Scheme III, a compound of formula VI, which is a known compound or can be prepared according to known procedures, is hydrogenated to yield a compound of formula Va. More particularly, the reaction is carried out with a catalyst, for example, palladium on carbon, in a solvent such as a lower carboxylic acid, preferably acetic acid, at a temperature in the range of about 20° C. to about 100° C., preferably at 25° C., and at an increased pressure, preferably 50 psi. The resulting compound of formula Va can be recovered utilizing conventional methods.

The compound of formula Va is then converted to its acyl derivative of formula V utilizing any suitable acylating agent, for example, a lower acyl halide or anhydride, preferred is acetic anhydride, in a suitable base, for example, a lower alkylamine or the like, preferred is pyridine, at a temperature in the range from about 0° C. to about 150° C., preferably at 25° C. The resulting compound of formula V is recovered using conventional methods.

The compounds of formula I possess an asymmetric carbon atom and, therefore, they are ordinarily obtained as racemic mixtures. The resolutions of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, when it is hydrogen, with an optically active resolving agent, for example, an optically active base, such as d-(+)- or 1-(−)-α-methylbenzylamine. The formed diastereomeric salts are separated by selective crystallization and converted to the corresponding optical isomer. Thus, the invention involves the use of racemates of the compounds of formula I, as well as their optically active isomers (enantiomers).

Further details and more specific methods of preparation for the compounds of formula I are found in the aforementioned South African patent publication.

Topical pharmaceutical compositions in which the described anti-inflammatory compounds of formula I can be incorporated may vary widely in type and include ointments, creams, lotions, gels, and so forth. In general, the solutions, ointments and creams which are useful in accordance with this invention include formulations having absorbable, water soluble or emulsion-type bases, such as petrolatum, lanolin, polyethylene glycols, or the like.

Suitable solutions will contain the compound dissolved in a pharmaceutically acceptable solvent, such as polyethylene glycol, or the like.

Suitable lotions will be liquid preparations which can vary from true solutions to aqueous or hydroalcoholic formulations containing finely divided particles. These lotions can contain suspending or dispersing agents such as cellulose derivatives, for example, methyl cellulose, ethyl cellulose, or the like.

The gels will typically be semi-solid preparations made by gelling a solution or suspension of the compound in a suitable hydrous or anhydrous vehicle, using a gelling agent such as a carboxy polymethylene, or the like, and thereafter neutralizing it to proper consistency with an alkali metal hydroxide, for example, sodium hydroxide, and an amine, for example, polyethylenecocoamine.

The topical pharmaceutical compositions of this invention can also be formulated to include conventional supplementary ingredients such as preservatives, stabilizers, wetting agents, emulsifying agents, buffers, and so forth, in conventional amounts adjusted for particular requirements and which are readily determinable by those skilled in the art.

By way of further description, a number of suitable topical compositions in accordance with this invention are provided among the examples.

Typical dosage forms of the composition of the invention will contain the described compounds in amounts from about 0.1 to about 10 percent by weight, and more usually from about 0.5 to about 5 percent by weight, based on the total weight (100%) of the composition. The minimum or smallest amount necessary to be effective in a given case may vary, depending on the severity of the condition, age of the subject being treated, and potency, duration and concentration of the particular compound being used as the active ingredient. In all cases the amount which is anti-inflammatory should be sufficient to reduce the symptoms of the inflammation and, more specifically, to lessen skin redness, itching, scaling, swelling, and so forth, at the site of inflammation. In practice, the method of the invention is being carried out by spreading, gently rubbing or spraying the ointment, cream, lotion, gel, or the like, in a thin layer over the inflamed area, from one to four times each day, or as needed, depending on the desired dose in a warm-blooded animal.

The useful anti-inflammatory activity of this invention is demonstrated in warm-blooded animals using the following procedures.

I. VASCULAR PERMEABILITY TEST, IN VIVO (RATS AND GUINEA PIGS)

(a) Leukotriene (LTD$_4$) Alone

Male guinea pigs (Hartley strain) weighing 500 to 600 g and male rats (Sprague-Dawley strain) weighing 250 to 300 g were pretreated by the intraperitoneal injection of pyrilamine maleate (an antihistamine) in a dose of 50 mg per kg of body weight, and methylsergide maleate (a serotonin antagonist) in a dose of 50 mg/kg. After thirty minutes, the animals were anesthetized with urethane (1.6 g/kg). Using a syringe, 0.05 ml of a saline solution of a leukotriene (LTD$_4$) in varying concentrations of 0.2 to 200 micrograms per milliliter ($\mu$g/ml) was injected intradermally into each of the anesthetized animals in four different areas. Immediately afterwards, 1.0 ml (rat) or 1.25 ml (guinea pig) of Evans blue dye, in a concentration of 0.5% in saline solution, was injected into a tail vein of each rat or an ear vein (right ear) of each guinea pig. Thirty minutes later, the animals were sacrificed by cervical dislocation.

The increase in vascular permeability caused by the injected leukotriene was manifested by a noticeable migration of the Evans blue dye into the immediate area of each leukotriene injection point. To quantify this, the dorsal skin of the test animal was surgically removed, the long and short axes of each blue dye spot (wheal) was measured with a standard metric vernier caliper, and the average diameter was calculated from these measurements. The results are graphed in FIG. 1, with each point representing the mean wheal diameter ±S.E.M. for measurements on three guinea pigs or three rats, four leukotriene injection points per animal (for a total of 12 observations).

As shown in FIG. 1, after injection the leukotriene caused a dose dependent increase in the vascular permeability, as reflected by the migration of the dye through the blood vessels into the area of the leukotriene-injection points in the skin of both the guinea pigs and the rats.

(b) Leukotriene (LTD$_4$ and Inhibitors (Single Concentration, Time Variation)

Racemic-6-acetyl-7-[5-(4-acetyl-3-hydroxy-2-propylphenoxy)-pentyloxy]-3,4-dihydro-2H-1-benzopyran-2-carboxylic acid, in accordance with this invention, was evaluated for its ability to inhibit the increase in vascular permeability induced by the intradermal injection of a leukotriene. The test compound was administered to the same number of animals as before by applying one drop (50 microliters) directly on the skin surface of a 10% by weight solution of the test compound in dimethylsulfoxide (DMSO). This amounted to 5 mg of test compound per site of application. After applying the test compound, at the various time intervals indicated in FIGS. 2 and 3, the leukotriene (LTD$_4$) was injected intradermally in each topically pretreated skin area with 0.05 ml of a saline solution containing the leukotriene in a concentration of 8 micrograms per milliliter, which was equivalent to 0.4 microgram of leukotriene applied per injection site. Evans blue dye (0.5% in saline) was then injected intravenously into each animal, using the same procedure describd for Part (a), above. After thirty minutes the animals were sacrificed, the dorsal skins were removed, and the extent of dye migration was measured as above. The effectiveness of the test compound was calculated as the Percent (%) Inhibition of Leukotriene-Induced Permeability, as follows:

% Inhibition =

$$\frac{MWS \text{ of test compound treated} - MWS \text{ of control}}{MWS \text{ of control}} \times 100$$

where MWS=mean wheal size.

Figure 2:
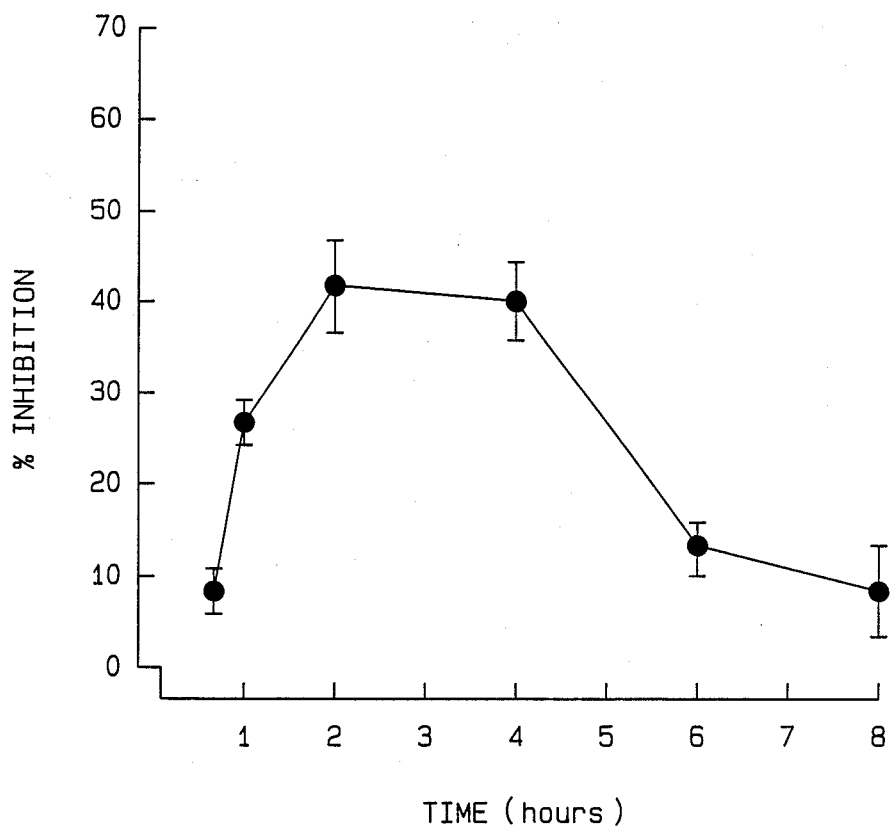
Figure 3:
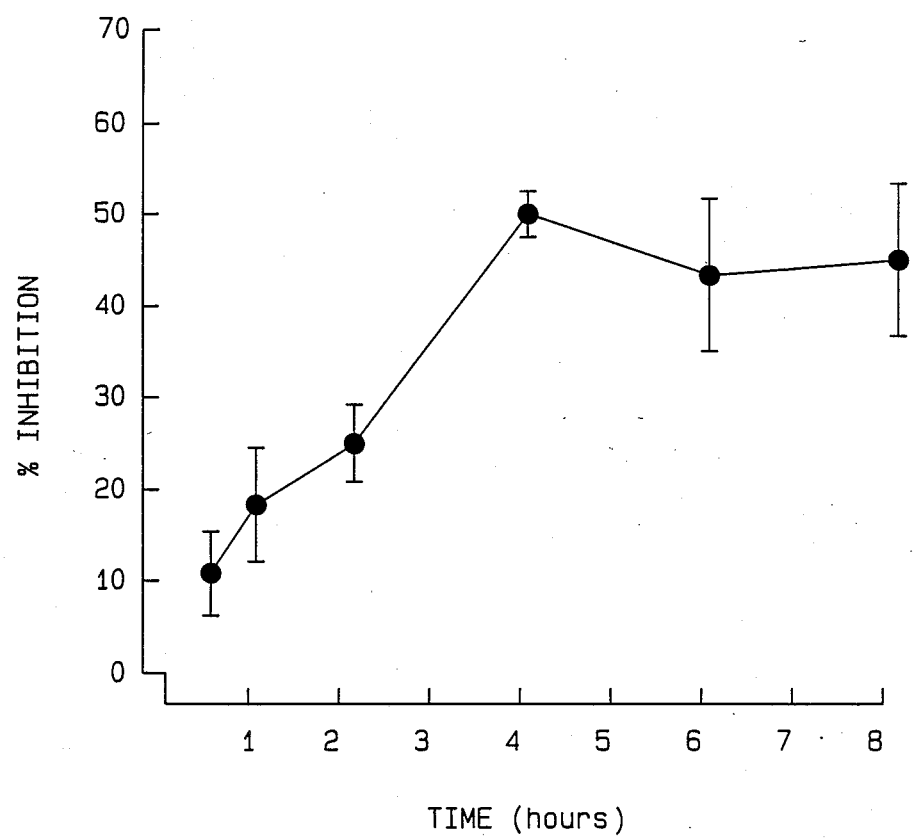

The Percent Inhibition for the test compound as a function of time, in both guinea pigs and rats, is shown in FIGS. 2 and 3, respectively.

As shown, the test compound inhibited leukotriene-induced vascular permeability, with peak activity being reached in guinea pigs after 2–4 hours and in rats somewhat later.

(c) LTD$_4$ and Inhibitors, (Variation of Concentration)

The procedure of Part (b) was repeated, except that the test compound was applied topically four hours prior to leukotriene injection, and the concentration of the test compound was varied as shown in Tables 1 and 2, where the results are also reported.

As shown, the test compound inhibited the leukotriene-induced vascular permeability increase in a dose-related manner.

TABLE 1

DOSAGE-RELATED TOPICAL ACTIVITY OF TEST COMPOUNDS IN RAT VASCULAR PERMEABILITY TEST

| Concentration (% in DMSO) | % Inhibition (± S.E.M.) |
|---|---|
| 2.5 | 28 ± 4 |
| 5.0 | 50 ± 6 |
| 10.0 | 59 ± 6 |
| 15.0 | ND |
| 25.0 | 67 ± 5 |

ND = not determined

TABLE 2

DOSAGE-RELATED TOPICAL ACTIVITY OF TEST COMPOUNDS IN PIG VASCULAR PERMEABILITY TEST

| Concentration (% in DMSO) | % Inhibition (± S.E.M.) |
|---|---|
| 1.0 | ND |
| 5.0 | 11 ± 3 |
| 10.0 | 33 ± 3 |
| 15.0 | 43 ± 4 |
| 25.0 | 49 ± 4 |

ND = not determined

II. MOUSE EAR EDEMA TEST (IN VIVO)

In this animal model system, the application of arachidonic acid to the ear results in the biosynthesis of the metabolic products 5-hydroperoxy-6,8,11,14-eicosatetraenoic acid (5-HETE), leukotriene B$_4$ (LTB$_4$), leukotriene C$_4$(LTC$_4$), 12-hydroperoxy-5,8,10,14-eicosatetraenoic acid (12-HETE), and prostaglandin E$_2$ (PGE$_2$) at the site of application, followed by the influx of neutrophils into the site and the rapid development of edema within 30 to 60 minutes (See, for instance, Young, Wagner and Spires, "Tachyphylaxis in 12-O-Tetracecanoylphorbol Acetate—And Arachidonic Acid-Induced Ear Edema," J. Invest. Dermatol. 80: 48 (1983), and Humes, Opas and Bonney, "Arachidonic Acid Metabolites in Mouse Ear Edema". Advances in Inflammation Research, 11: 57 (1986). Inhibitors of these metabolites and of their metabolic pathways also inhibit edema formation.

CD-1 male mice weighing 15 to 25 g were employed, and they were designated as follows: (1) Control Group, in which no arachidonic acid or test compound were to be applied, (2) Arachidonic Acid-Treated Group, in which no test compound was to be applied, and (3) Treated Group, in which the test compound was to be applied first, followed by the application of arachidonic acid. The test compound was again racemic-6-acetyl-7-[5-(4-acetyl-3-hydroxy-2-propylphenoxy)pentyloxy]-3,4-dihydro-2H-1-benzopyran-2-carboxylic acid.

In the case of the Group (3) animals, the test compound, dissolved in acetone, was applied to the dorsal surface of the right ear of the mouse with a 25-microliter pipettor, with the dose of the test compound being varied as shown in Tables 3 and 4. After 0.5 hour in some cases and 4 hours in others, the arachidonic acid was topically applied in the same manner as above to the pretreated ear areas. In each case of arachidonic acid application, an amount of 0.5 mg dissolved in 25 microliters of acetone was used. Application was made topically to the dorsal surface of the right ear with a 25-microliter pipettor. After one hour, the mice were sacrificed by carbon dioxide inhalation. A 6 mm-diameter standard biopsy punch was used to obtain a uniform tissue sample from the ear of each mouse so treated, and the tissue samples were weighed to the nearest 0.1 mg. The percent inhibition of ear edema formation was calculated as follows:

$$\frac{\text{Wt. of Arachidonic Acid Group} - \text{Wt. of Testing Group}}{\text{Wt. of Arachidonic Acid Group} - \text{Wt. of Control Group}} \times 100$$

The results are given in Tables 3 and 4. As shown, the test compound in accordance with this invention produced significant inhibition of edema when used in amounts up to 2 mg. both 0.5 and 4 hours prior to arachidonic acid application.

TABLE 3
TOPICAL ACTIVITY OF BENZOPYRAN AS INHIBITOR OF ARACHIDONIC ACID-INDUCED EAR EDEMA IN MICE

| mg of test compound applied[b] | % Inhibition (± S.E.M.)[a] | |
|---|---|---|
| | 0.5 Hour Pretreatment | 4 Hour Pretreatment |
| 0.1 | 19 ± 10 | 26 ± 9 |
| 0.2 | 21 ± 12 | 31 ± 12 |
| 0.5 | 42 ± 12 | 28 ± 9 |
| 1.0 | 63 ± 4 | 37 ± 7 |
| 2.0 | 65 ± 1 | 68 ± 7 |

[a]Eight mice were used for each determination.
[b]The amounts shown were each dissolved in 25 μl of acetone and applied as a solution.

EXAMPLE 1

TOPICAL FORMULATION (Solution)

| Ingredients | Amount, g/100 ml | | |
|---|---|---|---|
| | 1 g | 2.5 g | 5 g |
| racemic-6-acetyl-7-[5-(4-acetyl-3-hydroxy-2-propylphenoxy)pentyloxy]-3,4-dihydro-2H—1-benzopyran-2-carboxylic acid | 1 g | 2.5 g | 5 g |
| polyethylene glycol (PEG) 400, in quantity sufficient to make* | 100 ml | 100 ml | 100 ml |

*PEG 400 can be substituted by isopropyl myristate, neobee oil, or Capmul MCM 90 (Stokely - Van Camp Inc., mixture of $C_8$—$C_{10}$ mono- and diglycerides)

Procedure:
Dissolve racemic 6-acetyl-7-[5-(4-acetyl-3-hydroxy-2-propylphenoxy)pentyloxy]-3,4-dihydro-2H-1-benzopyran-2-carboxylic acid in the polyethylene glycol at room temperature in an appropriate container.

EXAMPLE 2

TOPICAL FORMULATION (Ointment, non-emulsion type)

| Ingredients | Amount, g/g | | |
|---|---|---|---|
| | 0.1 g | 0.5 g | 1 g |
| racemic-6-acetyl-7-[5-(4-acetyl-3-hydroxy-2-propylphenoxy)pentyloxy]-3,4-dihydro-2H—1-benzopyran-2-carboxylic acid | 0.1 g | 0.5 g | 1 g |
| white petrolatum, q.s. to make | 100 g | 100 g | 100 g |

Procedure:
Micronize racemic-6-acetyl-7-[5-(4-acetyl-3-hydroxy-2-propylphenoxy)pentyloxy]-2,4-dihydro-2H-1-benzopyran-2-carboxylic acid to 1–10 micron particle size range by air attrition, then levigate or mill into the white petrolatum.

EXAMPLE 3

TOPICAL FORMULATION (Cream)

| Ingredients | Amount, g/g | | |
|---|---|---|---|
| | 0.1 g | 0.5 g | 1 g |
| racemic-6-acetyl-7-[5-(4-acetyl-3-hydroxy-2-propylphenoxy)pentyloxy]-3,4-dihydro-2H—1-benzopyran-2-carboxylic acid | 0.1 g | 0.5 g | 1 g |
| white petrolatum | 30.0 g | 30.0 g | 30.0 g |
| mineral oil | 20.0 g | 20.0 g | 20.0 g |
| surfactant (Arlacel 83) | 6.0 g | 6.0 g | 6.0 g |
| surfactant (Myrg 52) | 2.0 g | 2.0 g | 2.0 g |
| polyethylene glycol 400 | 25.0 g | 25.0 g | 25.0 g |
| water, sufficient to make | 100.0 g | 100.0 g | 100.0 g |

Procedure:
Separate the ingredients into two different phases according to physical and chemical properties, incorporate phase 1 into phase 2 with stirring above room temperature in an appropriate container, and cool slowly to room temperature.

Other topical formulations in accordance with the present invention, in the form of emulsion-type ointments, lotions, gels, and so forth, are possible and can be made using standard known procedures for such purposes.

I claim:
1. A method for treating leukotriene-mediated dermal inflammation, which comprises topically administering to the affected area an effective anti-inflammatory amount of a compound of the formula

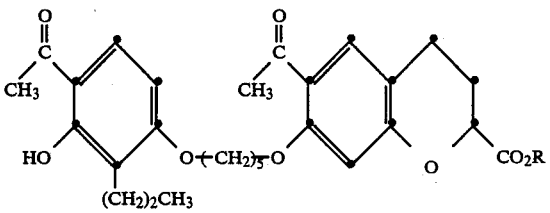

in which R is hydrogen or lower alkyl, an enantiomer thereof, or when R is hydrogen, a salt hereof.

2. The method of claim 1 used for treating psoriasis.

3. The method of claim 1, in which R is hydrogen.

4. The method of claim 1, in which R is alkyl having from 1 to 7 carbon atoms.

5. The method of claim 1, in which the compound is racemic-6-acetyl-7-[5-(4-acetyl-3-hydroxy-2-propylphenoxy)pentyloxy]-3,4-dihydro-H-1 -benzopyran-2-carboxylic acid.

6. The method of claim 1, in which the anti-inflammatory compound is applied from one to four times daily in a topical dosage form which contains from 0.1 to 10 percent by weight of the compound.

7. The method of claim 6, in which the dosage form contains from 0.5 to 5 percent by weight of the compound.

8. The method of claim 1 used for treating dermatitis.

9. The method of claim 1 used for treating eczema.

* * * * *